United States Patent
Demokritou et al.

(10) Patent No.: US 12,064,448 B2
(45) Date of Patent: Aug. 20, 2024

(54) METHODS FOR REDUCING BIOAVAILABILITY AND ABSORPTION OF INGESTED SUBSTANCES

(71) Applicants: Nanyang Technological University, Singapore (SG); President and Fellows of Harvard College, Cambridge, MA (US)

(72) Inventors: Philip Demokritou, Brookline, MA (US); Glen Deloid, Natick, MA (US); Kee Woei Ng, Singapore (SG); Say Chye Joachim Loo, Singapore (SG)

(73) Assignees: Nanyang Technological University, Singapore (SG); President and Fellows of Harvard College, Cambridge, MA (US)

( * ) Notice: Subject to any disclaimer, the term of this patent is extended or adjusted under 35 U.S.C. 154(b) by 803 days.

(21) Appl. No.: 16/762,845

(22) PCT Filed: Nov. 9, 2018

(86) PCT No.: PCT/US2018/060096
§ 371 (c)(1),
(2) Date: May 8, 2020

(87) PCT Pub. No.: WO2019/094769
PCT Pub. Date: May 16, 2019

(65) Prior Publication Data
US 2021/0030782 A1    Feb. 4, 2021

Related U.S. Application Data

(60) Provisional application No. 62/697,827, filed on Jul. 13, 2018, provisional application No. 62/584,504, filed on Nov. 10, 2017.

(51) Int. Cl.
A61K 31/717    (2006.01)
A61K 9/14    (2006.01)

(52) U.S. Cl.
CPC ............ A61K 31/717 (2013.01); A61K 9/146 (2013.01)

(58) Field of Classification Search
CPC .................................... A61K 9/48; A61F 5/00
See application file for complete search history.

(56) References Cited

U.S. PATENT DOCUMENTS

| | | | |
|---|---|---|---|
| 7,202,222 B2 | 4/2007 | Ramazanov et al. | |
| 9,149,064 B2 | 10/2015 | Zhao et al. | |
| 2008/0227753 A1 | 9/2008 | Lian et al. | |
| 2015/0299954 A1 | 10/2015 | Lian et al. | |
| 2017/0027168 A1* | 2/2017 | Heath | A61P 17/00 |
| 2017/0079926 A1* | 3/2017 | Costa | A61K 9/4808 |

FOREIGN PATENT DOCUMENTS

| | | |
|---|---|---|
| CN | 1884570 A | 12/2006 |
| CN | 103741532 A | 4/2014 |
| CN | 104381591 A | 3/2015 |
| CN | 106900853 A | 6/2017 |
| CN | 107059456 A | 8/2017 |
| CN | 111902131 A | 11/2020 |
| JP | 2016065116 A | 4/2016 |
| JP | 2021-502087 A | 1/2021 |
| KR | 10-2020-0097260 A | 8/2020 |
| WO | WO-2019094769 A1 | 5/2019 |

OTHER PUBLICATIONS

Dai Hongqi et al (CN 106900853 A, English Translated Document (Year: 2017).*
"European Application Serial No. 18876991.3, Extended European Search Report mailed Jul. 22, 2021", 9 pgs.
"European Application Serial No. 18876991.3, Response to Communication pursuant to Rules 161(2) and 162 EPC filed Nov. 2, 2020", 5 pgs.
"International Application Serial No. PCT/US2018/060096, International Preliminary Report on Patentability mailed May 22, 2020", 8 pgs.
Deloid, Glen M., et al., "Reducing Intestinal Digestion and Absorption of Fat Using a Nature-Derived Biopolymer: Interference of Triglyceride Hydrolysis by Nanocellulose", *ACS Nano*, vol. 12, (2018), 6469-6479.
Ji, Na, et al., "Interaction of cellulose nanocrystals and amylase: Its influence on enzyme activity and resistant starch content", *Food Chemistry*, vol. 245, (Nov. 5, 2017), 481-487.
"International Application Serial No. PCT/US2018/060096, International Search Report mailed Jan. 7, 2019", 2 pgs.
"International Application Serial No. PCT/US2018/060096, Written Opinion mailed Jan. 7, 2019", 6 pgs.
Deloid, et al., "Reducing Intestinal Digestion and Absorption of Fat Using a Nature-Derived Biopolymer: Interference of Triglyceride Hydrolysis by Nanocellulose", ACS Nano, vol. 12, (Jun. 6, 2018), 6469-6479.
"European Application Serial No. 18876991.3, Response filed Jan. 31, 2022 to Extended European Search Report mailed Jul. 22, 2021", 7 pgs.
"Chinese Application Serial No. 201880085838.1, Office Action mailed Jan. 27, 2022", (w/ English Translation), 27 pgs.

(Continued)

*Primary Examiner* — Layla D Berry

(74) *Attorney, Agent, or Firm* — Schwegman Lundberg & Woessner, P.A.

(57) ABSTRACT

Methods for reducing at least one of the bioavailability and absorption of at least one of ingested fat, carbohydrates, and unwanted substances from foodstuff in a subject are disclosed. The methods described herein include administering an amount of a nanobiopolymer, or combinations of nano-biopolymers, sufficient to reduce at least one of the bioavailability and absorption of ingested fat, carbohydrates, and unwanted substances to a subject, such as a human subject.

9 Claims, No Drawings

(56) References Cited

OTHER PUBLICATIONS

Lu, Qi-Lin, et al., "Research Progress of Nanocrystalline Cellulose", (w/ English Abstract), Guangzhou Chemical Industry, vol. 41, No. 20, (2013), 1-4.

Zhang, Wei, "The Preparation of Nanosized Chitosan and Its Hypolipidemic Activity", (w/ English Abstract), Full-text Database of Chinese Excellent Doctoral Dissertations, Engineering Science and Technology Series I, No. 9, (2013), B02-74, 8 pgs.

"Chinese Application Serial No. 201880085838.1, Office Action mailed Dec. 13, 2022", W/ English Translation, 17 pgs.

"Chinese Application Serial No. 201880085838.1, Response filed Mar. 28, 2023 to Office Action mailed Jan. 27, 2022", w/ English claims, 21 pgs.

"Chinese Application Serial No. 201880085838.1, Response filed Aug. 11, 2022 to Office Action mailed Jan. 27, 2022", w/ English claims, 11 pgs.

"Japanese Application Serial No. 2020-525858, Notification of Reasons for Refusal mailed Mar. 7, 2023", w/ English Translation, 10 pgs.

Bokura, Hirokazu, et al., "Long-term Efficacy and Safety of Chitosan for Hypercholesterolemia", Japanese Dietary Fiber Study Group Magazine, 2002, and vol. 6, No. 2, (2002), 61-71.

Ikemoto, Shinji, "Cholesterol-lowering Effects of Dietary Fiber", Japanese Dietary Fiber Study Group Magazine, 2000 and vol. 4, No. 1, (2000), 1-8.

Lu, Hongjia, "Efficacies of Sweet Potato Dregs Cellulose Nanocrystal on Reducing Blood Glucose and Blood Lipid as well as the Research thereon for Molecular Mechanisms", (w/ English Abstract), Doctoral Dissertation of Southwest University, (2015), 40 pgs.

Takahashi, Tokio, et al., "Effect of Soybean Curd Refuse on Cholesterol Metabolism in Rats", Journal of Japanese Society of Nutrition and Food Science, 1986, and vol. 39, No. 5, (1986), 377-384.

\* cited by examiner

US 12,064,448 B2

METHODS FOR REDUCING BIOAVAILABILITY AND ABSORPTION OF INGESTED SUBSTANCES

CROSS-REFERENCE TO RELATED APPLICATIONS

This application is a U.S. National Stage Application under 35 U.S.C. 371 from International Application Serial No. PCT/US2018/060096, filed on Nov. 9, 2018, and published as WO 2019/094769 A1 and published on May 16, 2019, which claims the benefit of U.S. Provisional Appl. Nos. 62/584,504, filed Nov. 10, 2017 and 62/697,827, filed Jul. 13, 2018, all of which are incorporated by reference as if fully set forth herein in their entirety.

STATEMENT OF GOVERNMENT SUPPORT

This invention was made with government support under grant ES026946 awarded by the National Institutes of Health. The government has certain rights in the invention.

BACKGROUND

Many foods contain nanosize particles, either naturally occurring in the food, generated during processing, or introduced from the environment. Engineered nanomaterials (ENMs) are increasingly added intentionally to take advantage of their unique properties to improve food quality or safety. Until now, however, the use of ENMs in food as a modifier of the bioavailability and absorption of ingested substances, including fat, has not been explored.

DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

The instant disclosure relates to a method for reducing at least one of the bioavailability and absorption of at least one of ingested fat (e.g., triglycerides and free fatty acids), carbohydrates, and unwanted substances from foodstuffs in a subject. Subjects are animals including but not limited to those belonging to the vertebrate group amniota, which includes all mammals (including but not limited to humans, non-human primates, cows, pigs, horses, dogs, cats, mice, rats, rabbits, and guinea pigs) as well as all birds and reptiles. The method comprises oral administration of an amount of a nanobiopolymer sufficient to reduce at least one of the bioavailability and absorption of ingested fat, carbohydrates, and unwanted substances to a subject.

As used herein, the term "unwanted substances" includes, but is not limited to, glucose and toxins, such as heavy metals and pesticides, though in some contexts, fat and carbohydrates could be considered "unwanted substances." Heavy metals are generally defined as metals with relatively high densities, atomic weights, or atomic numbers. Heavy metals are relatively uncommon in the earth's crust but are present in many aspects of modern life. Examples of heavy metals, include mercury (Hg), cadmium (Cd), arsenic (As), chromium (Cr), thallium (Tl), and lead (Pb), all of which can be highly poisonous.

The amount of a nanobiopolymer sufficient to reduce at least one of the bioavailability and absorption of at least one of ingested fat, carbohydrates, and unwanted substances from foodstuff can be any suitable amount, such as from as little as or less than about 0.01% to as high as or higher than about 10% by weight of the foodstuff. For example, the amount of a nanobiopolymer sufficient to reduce at least one of the bioavailability and absorption of at least one of ingested fat, carbohydrates, and unwanted substances from foodstuff can be from about 0.75% to about 5%, about 0.75% to about 1.5%, about 1% to about 2%, about 1% to about 3%, about 2.5% to about 5% or about 0.9 to about 1.5% by weight of the foodstuff.

The amount of a nanobiopolymer sufficient to reduce at least one of the bioavailability and absorption of at least one of ingested fat, carbohydrates, and unwanted substances from foodstuff can be any suitable amount, such as an amount that reduces the at least one of the bioavailability and absorption of at least one of ingested fat, carbohydrates, and unwanted substances by at least about 10%, at least about 15%, at least about 20%, at least about 25%, at least about 30%, at least about 35%, at least about 40%, at least about 50%, at least about 60% or more of the at least one of the bioavailability and absorption of at least one of ingested fat, carbohydrates, and unwanted substances. For example, the amount of a nanobiopolymer sufficient to reduce at least one of the bioavailability and absorption of at least one of ingested fat, carbohydrates, and unwanted substances from foodstuff can be the amount sufficient to reduce the at least one of the bioavailability and absorption of at least one of ingested fat, carbohydrates, and unwanted substances by about 10% to about 99%, about 20% to about 50%, about 30% to about 90%, about 35% to about 80%, about 50% to about 90% or about 40% to about 90% of the at least one of the bioavailability and absorption of at least one of ingested fat, carbohydrates, and unwanted substances.

The at least one of the bioavailability and absorption of ingested fat can be reduced by any mechanism, such as (i) reduction in translocation of substances such as triglycerides, glucose or toxins, if the substance crosses the subject's intestinal epithelium; (ii) modulating activity of digestive enzymes including, proteases, amylases, and lipases; (iii) otherwise inhibiting the hydrolysis of triglycerides, polypeptides, or starch polymers; or combinations of two or more of the mechanisms (i)-(iii) or other mechanisms. The instant disclosure, therefore also relates to a method for reducing serum levels of triglycerides, glucose or other ingested substances; the method comprising: administering an amount of nanobiopolymer sufficient to reduce serum levels of triglycerides, glucose or other ingested substances to a subject.

As used herein, the term "nanobiopolymer" generally refers to a nanomaterial composed of biopolymers. The nanomaterials can be in the form of nanofibers, nanoplates, nanoparticles, and the like, and combinations thereof, such as fibrillar nanocellulose made by mechanical milling of, e.g., wood pulp, or nanocrystalline cellulose made by chemical means or combinations thereof.

When the nanomaterials are in the form of nanofibers, the nanofibers can have any suitable aspect ratio (e.g., the ratio of one dimension, such as width or length, to another dimension, such as thickness or diameter) such as at least about 0.5, at least 0.7, at least 0.9, at least 1 or greater. For examples, nanofibers can have an aspect ratio of length to diameter greater than one and a diameter ranging from 1 nm up to about 1000 nm, up to about 500 nm, or even up to 100 nm, including from about 15 nm to about 500 nm.

"Nanoplates" generally refers to a nanomaterial having the general shape of a plate having two large dimensions (length and width) and one small dimension (thickness). For example, nanoplates can have a thickness of less than about 1000 nm, less than 100 nm or even less than 10 nm; or from about 10 nm up to about 1000 nm.

"Nanoparticles" generally refers to a nanomaterial any suitable morphology including substantially spherical. But the nanoparticles can also have an irregular or substantially amorphous shape. In some examples, that include a plurality of nanoparticles, a major portion of the individual nanoparticles can be substantially spherical. For example, approximately 80% to about 100% of the nanoparticles can have a substantially spherical morphology.

A particle size of the individual nanoparticle is in a range of from about 20 nm to about 200 nm, about 40 nm to about 60 nm, or less than, equal to, or greater than about 20 nm, 30, 40, 50, 60, 70, 80, 90, 100, 110, 120, 130, 140, 150, 160, 170, 180, 190, or about 200 nm, such as a diameter from about or less than about 1 nm to about or greater than about 250 nm.

The "particle size" of the individual metallic nanoparticle refers to the largest dimension of the nanoparticle. For example, the largest dimension of the nanoparticle can refer to a diameter, width, or height of the nanoparticle. In some examples including a plurality the nanoparticles, a first nanoparticle can have a particle size in a largest dimension that is different from a particle size in a largest dimension of a second nanoparticle.

Nanobiopolymers contemplated herein include, but are not limited to, cellulose, including cellulose nanofibers and cellulose nanocrystals, wherein the cellulose has the formula:

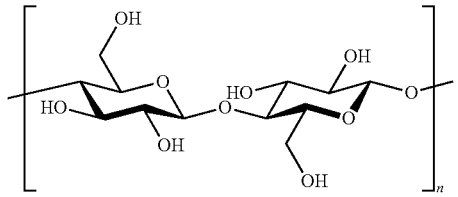

where n is the degree of polymerization and represents the number of glucose groups.

Nanobiopolymers contemplated herein also include, but are not limited to, chitosan, kefiran, and okara. Chitosan includes a polysaccharide that is obtained from the hard outer skeleton of shellfish, including crab, lobster, and shrimp. Kefiran includes an exopolysaccharide secreted by lactic acid bacteria in Kefir. Okara includes polysaccharide derived from tofu/soy bean processing. Without wishing to be bound by any specific theory, it is believed that each of these biopolymers can provide large surface areas for interactions with soluble digestive molecules (e.g., enzymes, bile salts, etc.), cell surface biomolecules involved in digestion and absorption, and food components and toxins, which can result in modulation of digestion and absorption of specific target substances. Each of these biopolymers in its native form, as they occur in nature or as produced in nature, can have a distinct surface chemistry that can determine the extent and variety of these interactions and thus efficacy in modulation of a target substance(s), such as fat, carbohydrates, and unwanted substances, such as toxins.

In some instances, cellulose nanofibers and cellulose nanocrystals can be chemically modified such that the cellulose nanofibers or cellulose nanocrystals comprise at least one of alkyl, carboxy, carboxyalkyl, and hydroxyalkylated cellulose. Accordingly, cellulose nanofibers and cellulose nanocrystals can comprise at least one of cellulose esters and cellulose ethers.

Examples of cellulose esters include esters derived from organic acids, such as cellulose acetate, cellulose triacetate, cellulose propionate, cellulose acetate propionate, and cellulose acetate butyrate, where, e.g., cellulose (di)acetate has the general formula:

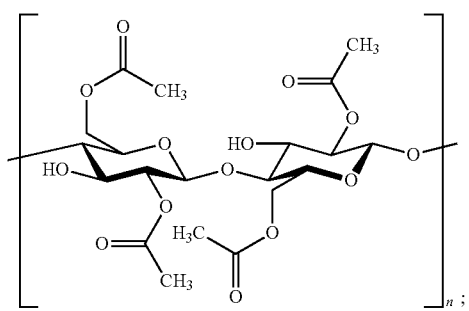

and Cellulose triacetate has the general formula:

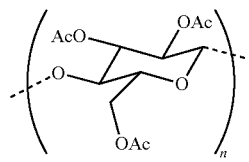

wherein "Ac" represented the group $OC(O)CH_3$.

Examples of cellulose ethers include those derived from alkyl halides (e.g., chloromethane and chloroethane), such as methylcellulose, ethylcellulose, and ethyl methyl cellulose; those derived from epoxides (e.g., ethylene oxide and propylene oxide), such as hydroxyethylcellulose, hydroxypropyl cellulose, hydroxyethyl methyl cellulose, hydroxypropyl methyl cellulose, and ethyl hydroxyethyl cellulose; and those derived from halogenated carboxylic acids (e.g., chloroacetic acid), such as carboxymethyl cellulose, and having the general formula:

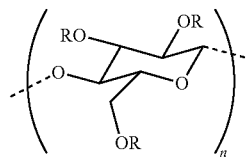

wherein R is H, alkyl (e.g., methyl or ethyl), hydroxyalkyl (e.g., $CH_2CH_2OH$), and carboxyalkyl (e.g., $CH_2CO_2H$).

The nanobiopolymers, such as the various celluloses described herein, can have a number average molecular weight (Mn) of at least about 10,000, at least about 20,000, at least about 30,000 or up to about 200,000. The weight average molecular weight (Mw) can be, for example, at least about 10,000, at least about 20,000, at least about 30,000 or up to about 200,000. The molecular weight distribution (Mw/Mn) is, for example, about 1.1 or more, about 1.4 or more or up to about 4.0. The molecular weight can be measured by gel permeation chromatography (GPC) using, for example, chloroform as a solvent (calibrated based on a polystyrene standard sample).

The nanobiopolymers described herein can be administered with or without the use of pharmaceutically acceptable excipients and carriers. A "pharmaceutical excipient" or a "pharmaceutically acceptable excipient" is a carrier, sometimes a liquid, in which a nanobiopolymer described herein can be formulated. The excipient generally does not provide any pharmacological activity to the formulation, though it can provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes, but is not limited to, any and all solvents, dispersion media, coatings, antibacterial and antifungal agents, isotonic and absorption delaying agents that are physiologically compatible. Pharmaceutically acceptable carriers include sterile aqueous solutions or dispersions and sterile powders for the extemporaneous preparation of sterile dispersions. Except insofar as any conventional media or agent is incompatible with the nanobiopolymers contemplated herein, use thereof in the compositions described herein is contemplated.

Oral forms of administration are contemplated herein. The nanobiopolymers described herein can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The compositions contemplated herein can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

The nanobiopolymers contemplated herein can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, beads, powders, gum, granules, particles, microparticles, dispersible granules, cachets, and combinations thereof.

Other compounds which can be included by admixture are, for example, medically inert ingredients (e.g., solid and liquid diluent), such as lactose, dextrose-saccharose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

The nanobiopolymer contemplated herein can be incorporated into the foodstuff; can be administered separately from the foodstuff; or can be incorporated into the foodstuff and administered separately from the foodstuff. For example, the nanobiopolymers described herein can be added to a noncomestible composition or non-edible product, such as supplements, nutraceuticals, and functional food products (e.g., any fresh or processed food claimed to have a health-promoting and/or disease-preventing properties beyond the basic nutritional function of supplying nutrients). The nanobiopolymer contemplated herein can also be added to animal feed and pet food.

For example, the nanobiopolymers described herein can be added to foodstuffs, such as food or beverage products or formulations. Examples of food and beverage products or formulations include, but are not limited to coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready to serve, semi condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready to cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category means beverages, beverage mixes and concentrates, including but not limited to, carbonated and non-carbonated beverages, alcoholic and nonalcoholic beverages, ready to drink beverages, liquid concentrate formulations for preparing beverages such as sodas, and dry powdered beverage precursor mixes. The Beverage category also include the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh (e.g., brewed), instant, combined coffee, liquid, ready-to-drink, soluble and dry coffee beverages, coffee beverage mixes and concentrates (syrups, pure, formulated, or in powder form; example of a "powder form" is a product comprising coffee, sweetener, and whitener all in powder form); tea, such as black, green, white, oolong, and flavored tea; and other hot drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products. The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The read meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi pack dairy ice cream, multi pack water ice cream, take home ice cream, take home dairy ice cream, ice cream desserts, bulk ice cream, take home water ice cream, frozen yoghurt, artisanal ice cream, dairy products, milk, fresh/pasteurized milk, full fat fresh/pasteurized milk, semi skimmed fresh/pasteurized milk, long life/uht milk, full fat long life/uht milk, semi skimmed long life/uht milk, fat free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners (e.g., dairy and non-dairy based creamers or whiteners for coffee beverages), powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf stable desserts, dairy based desserts, soy based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars; energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow on milk formula, toddler milk formula, hypoallergenic milk formula, prepared baby food, dried baby food, other baby food, spreads, jams and preserves, honey, chocolate spreads, nut based spreads, and yeast-based spreads. Examples of comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Examples of comestible compositions also include breakfast cereals, sweet beverages or solid or liquid concentrate compositions for preparing beverages. Examples of comestible compositions also include coffee flavored food (e.g., coffee flavored ice cream).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed can be resorted to by those of ordinary skill in the art, and that such modifications and variations are considered to be within the scope of embodiments of the present disclosure The invention is now described with reference to the following Examples. The following working examples therefore, are provided for the purpose of illustration only and specifically point out certain embodiments of the present invention, and are not to be construed as limiting in any way the remainder of the disclosure. Therefore, the examples should be construed to encompass any and all variations which become evident as a result of the teaching provided herein.

EXAMPLES

The present invention can be better understood by reference to the following examples which are offered by way of illustration. The present invention is not limited to the examples given herein.

Materials and Methods

Nano-sized cellulose materials used included two sizes of fibrillar nanocellulose (CNF 50 nm and CNF 80 nm) and cellulose nanocrystals (CNC 25 nm). As control/comparator fibers, micron-scale cellulose (CMF) synthesized from the same fiber, wheat dextrin fibers, and psyllium husk fibers were also included in this study.

Preparation of Food Models and Combination with Test Fibers.

Heavy cream, mayonnaise and coconut oil were purchased from a supermarket. Corn oils was purchased from Sigma, Inc. These aforementioned fat food models were combined with nanocellulose or other control fibers including psyllium husk (Sigma) and wheat dextrin (Sigma) or the lipase inhibitor orlistat (Sigma). To combine test materials with cream, water, cream and the test material were combined to achieve the desired final concentrations of each, and the mixture was vortexed for 30 seconds. To combine test fibers with corn oil, the oil and water components were first combined and homogenized at high speed for 1 minute. Fibers or orlistat were then added to the emulsion and the mixture was vortexed for 30 seconds.

In Vitro Digestion.

In vivo simulated digestion was performed using a 3-phase (mouth, stomach, small intestine) method. Briefly, in the mouth phase of the gastrointestinal tract (GIT) simulator, the nano-enabled food was mixed with a simulated saliva fluid and incubated at 37° C. for 10 seconds. The resultant mouth digesta was then combined and incubated with a simulated gastric fluid and incubated for 2 hours at 37° C. on an orbital shaker to complete the stomach phase. For the small intestinal phase, the stomach digesta was combined with bile salts and proteins simulating intestinal fluid, and incubated at a constant pH of 7.0. The constant pH of 7.0 was maintained using a pH Stat device, and the amount of NaOH titrant added as a function of time was tracked. Free fatty acid (FFA) at the beginning of the intestinal phase (before addition of lipase) and in the final digesta was measured using a fluorometric assay kit (Cayman Chemical Cat #700310).

In Vitro Biokinetics.

Biokinetics of triglyceride (TG) and FFA were assessed using a triculture model of the small intestinal epithelium grown on transwell inserts. The development and methods for generating the triculture model was previously described in detail. Caco-2, HT-29MTX, and Raji B cells were obtained from Sigma, Inc. Caco-2 and HT29-MTX cells were grown in high-glucose DMEM supplemented with 10% heat-inactivated fetal bovine serum (FBS), 10 mM HEPES buffer, 100 IU/ml Penicillin, 100 μg/ml Streptomycin and non-essential amino acids (1/100 dilution of 100× solution, ThermoFisher). Raji B cells were cultured in RPMI 1640 media supplemented with 10% FBS, 10 mM HEPES buffer, 100 IU/ml Pennicillin and 100 μg/ml Streptomycin. Caco-2 and HT-29MTX cells were trypsinized and resuspended in DMEM media at $3 \times 10^5$ cells/cm$^3$, and combined in a ratio of 3:1 (Caco-2:HT29-MTX). 1.5 ml of the cell mixture was seeded in the apical chamber, and 2.5 ml of complete DMEM media was added to the basolateral compartment of a 6 well transwell plate (Corning). Media was changed after four days and subsequently every other day until day 15. On day 15 and 16 the media in the basolateral compartment was replaced with 2.5 ml of a suspension of Raji B cells at a concentration of $1 \times 10^6$ cells/ml in 1:1 DMEM:RPMI complete media. Biokinetics experiments were performed on day 17.

The final digesta from simulated digestions were combined with DMEM media in a ratio of 1:3, and 1.5 ml of the mixture was applied to the apical surface of the triculture cells. At 2 and 6 hours after addition of the digesta mixture, FFA in the basolateral fluid was measured using a fluorometric assay kit (Cayman Chemical Cat #700310), and TG was measured using a colorimetric assay kit (Cayman Chemical, Cat #10010303). Transepithelial electrical resistance (TEER) was measured using an EVOM2 Epithelial Volt/Ohm Meter with a Chopstick Electrode Set (World Precision Instruments) before addition of digesta and at 2 and 6 hours to ensure maintenance of an intact monolayer throughout the experiments.

In Vivo Evaluation of Effects of CNF on Fat Absorption Using a Rat Model.

The protocols used in this study were approved by the Harvard Medical Area Animal Care and Use Committee. Male Wistar Han rats (12 weeks old) were obtained from Charles River Laboratories (Wilmington, MA) and were housed in standard microisolator cages under controlled conditions of temperature, humidity, and light at the Harvard Center for Comparative Medicine. They were fed commercial chow (PicoLab Rodent Diet 5053, Framingham, MA) and were provided with reverse-osmosis purified water ad libitum. The animals were acclimatized in the facility for 7 days before the start of experiments.

Rats were fasted for 24 hours before the experiment. Each rat was anesthetized with isoflurane (Piramal Healthcare, Bethlehem, PA) and weighed. The cream or cream with CNF test suspension was delivered to the stomach via the esophagus using a 4-inch, 19G gavage needle with 2.25 mm ball tip (n=5 rats/group). The volume dose was 10 ml/kg. Venous blood samples (100 μL) were collected via the tail vein before and 1, 2 and 4 hours post-gavage. Blood samples were allowed to clot, then serum was separated by centrifugation at 5000×g for 10 minutes. Serum triglycerides were measured using a colorimetric assay kit (Cayman Chemical, Cat #10010303).

DMD Simulations

DMD is a subclass of molecular dynamics (MD) which employs several improvements in calculation efficiency, including an implicit solvent model, discretized potential functions, and re-calculation of atomic ballistic equations only when atoms have participated in a collision.[1] These features yield significant gains in calculation speed and efficiency, allowing for the simulation of larger molecular systems on longer time scales. Interatomic potentials include electrostatic, van der Waals (VDW), hydrogen bond, and solvation interactions. The Debye-Hückel approximation was used to model electrostatic screening, with a Debye length of 10 Å, corresponding to a solution ionic strength of approximately 100 mM×e$^2$. Solvation energy in these implicit solvent simulations was calculated using the Lazaridis-Karplus EEF1 (Effective Energy Function 1) model.[2]

Systems were modeled in all-atom DMD simulations with the MedusaScore force field,[3] which was previously parameterized on a large set of ligands and is transferrable to different molecular systems. The predictive power of MedusaScore has been validated in various benchmark studies, including recent CSAR (community structure-activity resource) blind ligand-receptor docking prediction exercises[4-5] where the performance of MedusaScore was among the best approaches in predicting the near-native ligand-binding poses and binding affinities.

Simulations were carried out in a simulation box size of 300 Å$^3$ with periodic boundary conditions. Unless otherwise noted, the temperature for each simulation was 0.603 kcal/(mol·$k_B$), which corresponds approximately to 37° C. Constant temperature was maintained using the Anderson thermostat.[6] After initialization, energy minimization was carried out for 1000 time steps of approximately 500 ps each. Production simulations were subsequently run for 500,000 time steps (approximately 25 ns). Time-dependent data was then extracted over the entire simulation for estimating the energy of binding (ΔE) and the number of atomic contacts between simulation constituents. Two atoms were defined as being in contact when within 6.5 Å of each other. All simulations were carried out on the Duke Compute Cluster, housed at Duke University. Each simulation was carried out on a single CPU core and completion times ranged from 3 to 130 hours.

The initial structure of human pancreatic lipase was obtained from the Protein Data Bank (PDB, entry 1eth).[7] All other molecules were constructed using the Avogadro molecular builder (v 1.1.1),[8] and included all heavy atoms and hydrogens. For those species with potentially charged moieties, a pH of 7.4 was assumed and sodium ions were incorporated into the simulation to balance the system net charge. Triglyceride micelles were pre-formed before introducing them into simulation systems by first simulating 9 palmitic acid triglycerides in a 3×3 grid (molecules not initially in contact with each other) and allowing the micelle to self-assemble over 300,000 time steps. This micelle was subsequently used in all appropriate simulations, and all triglyceride molecules were allowed to move freely and independently.

To estimate the binding energies, the potential energy (E) of the unbound system was obtained by calculating the mean and standard deviation values for all time points where the constituents were far from each other. Two molecules were considered bound when the value of interatomic contacts was non-zero. During all such time points, again the mean and standard deviations of the potential energy of the bound state were calculated. These two mean values were then used to calculate the ΔE of binding.

Cellulose Nanofiber Formation

A model cellulose nanofiber was formed from a set of 9 identical cellulose polymers. Each polymer was constructed from 40 repeating Glucose units. Because cellulose fibers are constructed primarily through a hydrogen bond network, such a network was allowed to self-assemble by performing a series of temperature-cycle simulations. The nine identical polymers were first initialized in a parallel 3×3 grid and performed a 500,000 time step simulation at a temperature of 0.1 kcal/(mol·$k_B$). This low temperature allowed for an initial set of hydrogen bonds to form among all 9 polymers. Additional simulations were subsequently performed for 300,000 time steps with temperature increasing by 0.15 kcal/(mol·$k_B$) each simulation until reaching a temperature of 0.55 kcal/(mol·$k_B$), after the temperature was decreased in the same manner. This cycle was repeated three full times. The temperature was increased slowly to break some fraction of the initial hydrogen bonds, and then lowered again to allow a new bond network to form. Each cycle resulted in a more complete network and lower net system potential energy. Effectively, the temperature cycles allowed the fiber system to reach a local energy minimum, and raising the temperature forced the system out of this local minimum. Repeated cycles resulted in the system sampling many possible configurations until the lowest possible energy was found for the system. The process was terminated after three cycles, as further temperature cycles provided only nominal decreases in net system potential energy. The result was a self-assembled cellulose nanofiber 19 nm long, approximately 4.5 nm high and 3.5 nm wide with a robust hydrogen bond network. The fiber was held static in subsequent simulations to preserve this self-assembled state, as it was assumed much longer fibers would be more difficult to break apart in solution than this short segment.

SUMMARY

Described herein are examples where nanobiopolymers, specifically nanocellulose (NC), was added to fatty food to observe the nanobiopolymer's effect, on among other things, the activity of pancreatic lipase, thereby substantially reducing the bioavailability and absorption of ingested fat. The ability of the nanobiopolymer to reduce lipase action on triglycerides (TGs) was initially observed in an in vitro simulated small intestinal digestion experiments employing a pH Stat device to maintain pH at 7.0. In this method, the pH is maintained at a constant value of 7.0 by adding NaOH titrant as needed. The pH is driven down by hydrolysis of fatty acids from triglycerides by pancreatic lipase. Thus, the amount of titrant required to maintain the pH at 7.0 can be used to determine the extent of TG hydrolysis and the amount of free fatty acids (FFA) released. During digestion of a fatty food model (e.g., heavy cream) a significant decrease in NaOH titrant used was observed when nanocellulose was included in the food. In addition, FFA measured at the end of digestion using a fluorometric assay were significantly reduced. Moreover, when the resulting digestate were applied to the apical surface of an in vitro triculture model of the intestinal epithelium, translocation of both FFA and TG were significantly reduced, thus confirming the data from digestion experiments. Finally, in in vivo experiments with rats it was observed that serum TG one hour after a single gavage meal of heavy cream were substantially reduced when NC was included in the meal, further confirming the ability of NC to inhibit fat absorption.

In total, the nature-derived NC developed and used in this study as the potential to be used either as a food additive, or as a stand-alone supplement taken with fatty meals, to provide a safe and effective measure for reducing fat absorbed from a meal, which could help with weight loss and improve health.

Example 1

In order to assess the effect of NC and other fiber types used as control/comparator materials on lipase activity (FFA release and thus bioavailability of fat), a high fat food model (heavy cream) with a final fat concentration of 13.3%, with or without 0.75% w/w of fiber (or positive control lipase inhibitor orlistat at 4.8 mg/ml) was processed using a 3-phase simulated digestion method. In terms of fatty acids released as determined by pH-stat titration during the small intestinal phase, the lipase inhibitor orlistat (4.8 mg/ml) nearly completely eliminated lipase activity (91.5% reduction, p<0.0001) as indicated by NaOH titrant used and percentage of total free fatty acids released during digestion. The three nano-scale NC materials, CNC, 80 nm CNF and 50 nm CNF, also caused substantial and significant reduction in NaOH used and percent of total fatty acids released. Of these materials, the strongest effect was seen with 50 nm CNF, which reduced fatty acid hydrolysis by 48.4% compared to control (p<0.0001), but substantial and significant effects were also observed with 80 nm CNF (40.6% reduction, p<0.0001) and CNC (34.4% reduction, p<0.0001). In contrast, micron-scale cellulose caused a marked and significant increase in FFA hydrolysis (38.4% increase, p<0.0001). Dextran fibers also resulted in a modest but significant increase in FFA hydrolysis (15.8%, p<0.05), and psyllium husk fibers had no significant effect. These findings suggest that the interference of triglyceride digestion is specific to nano-scale cellulose materials.

Direct fluorometric assay of FFAs was performed on digesta with and without 50 nm CNF to corroborate the less-direct pH Stat digestion results. By this method small amounts of FFA were present at the start of small intestinal digestion phase (prior to addition of lipase), with no significant difference between FFA concentrations in digesta with 50 nm CNF (817 μM) and without CNF (758 μM). Following addition of lipase and subsequent two hours of digestion, FFA increased to an average of 20,567 μM in digesta without CNF, and 8,954 μM in digesta with 50 nm CNF, representing an average reduction of 56%, consistent with pH stat results. Although these results did not reach statistical significance due to differences in final FFA between experiments, a substantial reduction was observed all individual experiments (51%, 23%, and 69%).

To assess the effect of food model and/or fat type, simulated digestions were performed with several different food models (heavy cream, mayonnaise, coconut oil, and corn oil, all at initial 13.3% total fat) with and without 0.75% w/w of 50 nm CNF. The strongest effect in vitro was observed with the heavy cream food model (50% reduction, p<0.0001). Smaller effects were observed for mayonnaise (19% reduction, p<0.001), corn oil emulsion (12.8% reduction, p<0.05), and coconut oil emulsion (11.2% reduction, p>0.05). These results suggest that the fat type or other components of the food model partly determine the extent of the interference of fat digestion by CNF. The degree of fatty acid saturation, however, does not appear to be a major factor, since the highest fraction of saturated fatty acids among the food models tested occur in heavy cream (65%) and coconut oil (90%), for which CNF had the largest and smallest effects, respectively, while mayonnaise and corn oil contain mostly unsaturated fats.

Example 2

In order to test whether the observed reduction in TG digestion and FFA release during digestion with CNF would affect movement of TG and FFA across the epithelium (fat absorption), the digesta from the heavy cream simulated digestions was applied to the apical compartment of a triculture small intestinal epithelial model, and TG and FFA concentrations were measured in the basolateral compartment at 2 and 6 hours. At both 2 and 6 hours, FFA concentration in the basolateral compartment was reduced by >50% by the presence of CNF (p<0.05 at 2 hours). Likewise, at both 2 and 6 hours, TG concentration in the basolateral compartment was reduced by 30% (p<0.05 at 2 hours).

Example 3

In order to confirm the gastrointestinal tract (GIT) simulation experiments and the aforementioned gut epithelial cellular data and asses whether nanocellulose would affect fat absorption from a high fat meal in an animal model, rats were gavaged with 3 mL of heavy cream with or without 1% 50 nm CNF, and blood drawn at 0, 1, 2, and 4 hours post gavage for TG analysis. Prior to gavage (0 hours) mean serum TG was the same in both groups of rats. At one hour post gavage, on average, serum triglyceride concentrations were 30% lower in rats that received CNF with the heavy cream gavage. At two hours post gavage serum TG was 15% lower in animals that received CNF. At 4 h post gavage mean TG levels were again identical between groups. The differences in TG between groups at 1 and 2 hours are consistent with the in vitro digestion and biokinetics results.

Example 4

In order to provide mechanistic insights into the observed nanoscale phenomena, molecular dynamic (MD) were performed to assess binding kinetics of certain biomolecules to nanocellulose fibers. Simulations consisting of three temperature cycles resulted in a self-assembled cellulose nanofiber. This fiber was approximately 19 nm long, 4.5 nm high, and 3.5 nm wide. These dimensions ensured that the fiber was much longer than individual fatty acids and triglycerides as well as triglyceride micelles (3.0 nm diameter). This fiber was also significantly longer than the longest axis of pancreatic lipase (approx. 10 nm).

MD simulations were performed to examine the interactions between cellulose nanofibers and palmitic acid, palmitic triglycerides, and human pancreatic lipase enzymes. The resulting binding energies are presented in Table 1.

TABLE 1

| System | Cellulose Fiber Binding Energy (kcal/mol) |
| --- | --- |
| Palmitic Acid | −2.2 ± 2.3 |
| Palmitic Triglyceride | −4.4 ± 2.5 |
| Palmitic Micelle | −14.8 ± 2.2 |
| Pancreatic Lipase | −55 ± 41 |

Palmitic acid simulations included 3 free fatty acids to match the fatty acid content of triglyceride simulations, and triglyceride simulations consisted of both single molecule and micelle simulations.

Palmitic acid interacted with cellulose nanofibers weakly, with a binding energy of −2.2±2.3 kcal/mol. Because this binding energy was smaller in magnitude than the energy standard deviation due to thermal fluctuations, in addition to the highly transient nature of the interactions, it was considered that free palmitic acid was nonbinding with cellulose nanofibers. Palmitic triglycerides, however, exhibited statistically significant (−4.4±2.5 kcal/mol) binding energies with cellulose nanofibers. The interactions were noticeably more frequent and long-lived compared with palmitic acid-cellulose nanofiber interactions. Palmitic triglyceride micelles in turn exhibited the strongest interactions with cellulose nanofibers. These interactions were long-lived in that, after quickly making contact with the fiber surface, they did not leave the surface for the duration of the simulation. The interactions were also strong, with a binding energy of −14.8±2.2 kcal/mol, significantly higher than either of the previous two species.

Due to its large size and diverse residues, interactions between pancreatic lipase and cellulose nanofibers were significantly more complex than with fatty acids. While there are some clear correlations between system energy and number of interatomic contacts, there were also significant energy fluctuations in the free enzyme system. This was due to thermal fluctuations causing changes in the tertiary and secondary structures of the enzyme. These fluctuations caused the large standard deviation in the enzyme-nanofiber binding energy. However, in examining those binding events which correlated with decreases in net system energy, it was concluded that pancreatic lipase bound with cellulose nanofibers with a binding energy of −55±41 kcal/mol. This interaction was driven primarily through short-lived hydrogen binding combined with a limited number of more specific ligand—cellulose and VDW interactions. Therefore, while the binding energy for enzyme-nanofiber interactions were largest in magnitude, the short-lived nature of these interactions coupled with large thermal fluctuations of the system at the same simulation temperature, lead us to conclude that the cellulose nanofiber—micelle interactions were the most significant among the tested species.

Despite only moderate binding between cellulose nanofibers and pancreatic lipase, there were noteworthy changes to the enzyme's structure.

Multiple lines of in vitro and in vivo study that the addition of nanocellulose to a high fat meal reduces fat bioavailability and absorption by impeding digestion of triglycerides. This effect is nano-specific, as it did not occur when a micron-scale cellulose derived from same initial fiber was used. Furthermore, no effect was observed with the commercial micron-scale fibers wheat dextrin and psyllium husk. The effect was most pronounced with the 50 nm CNF (48.4% reduction), and slightly less pronounced with 80 nm CNF and CNC.

While not wishing to be bound by any specific theory, it is believed that there are many potential mechanisms for this effect. For example, CNF may bind to or sequester the lipids, coat lipid droplets, form a hydrogel around lipid droplets, or cause lipid droplets to flocculate, thus reducing access of either bile salts or lipase to triglycerides. Alternatively, CNF may bind to and alter the activity or availability of lipase, or bind to or sequester bile acids. Finally CNF may increase the viscosity of the food thus impeding diffusion of digestive components. The results of molecular dynamics studies presented above suggest an interaction between TG or TG micelles and NC fibers, and little or only weak interactions between nanocellulose and either lipase or bile acids, but an alteration in the tertiary structure of lipase. These findings suggests that the mechanism may involve sequestering or coating of TG by NC, or an alteration in lipase activity. However further studies are needed to identify the specific mechanism involved.

It was also observed that the effect of nanocellulose on fat digestion is dependent on the food model or fat type, being most striking with a heavy cream (milk fat), in which fat digestion and bioavailability was reduced by 48%, and less pronounced with mayonnaise, corn oil and coconut oil emulsions (19%, 12%, and 11% reductions, respectively). The reason for the difference between effects with different food models may be related to other components of the food models or differences in the types of fat. The degree of fatty acid saturation, however, does not appear to have an effect, since coconut oil and milk fat both have higher percentages of saturated fatty acids than corn oil or mayonnaise, but had the lowest (coconut oil) and highest (cream/milk fat) reductions in FFA hydrolysis in the presence of nanocellulose. The unique structure of milk fat might be in part responsible for the greater effect with this food model. Unhomogenized milk fat consists of TG globules coated by a lipid bilayer that is obtained during excretion by mammary glands. Upon homogenization (as the samples used in this study were), the lipid bilayer is disrupted and the globules are partially coated with casein micelles. It is possible that interactions between nanocellulose and remnants of the milk fat lipid bilayer or casein micelles enhance the sequestering of fat by nanocellulose, or one of the other possible mechanisms mentioned herein.

Example 5

Starch in foods exists as small granules (several micrometers in diameter) that are composed of multiple concentric alternating crystalline and amorphous layers containing polymers of glucose. The glucose polymers of starch include amylose (linear polymers connected by α 1-4 bonds) and amylopectin (branched polymers including both α 1-4 and α 1-6 linkages). Starch cannot be absorbed directly from the GIT. Only glucose monomers (and other sugar monomers) can be directly absorbed. Thus, in order for the caloric content of starch (glucose) to be made available for absorption, the amylose and amylopectin polymers contained within the starch granules must first be broken down to individual glucose molecules. This is accomplished through a combination of external processing (cooking), mechanical action (chewing) and enzymatic digestion. Cooking causes starch granules to swell with water and destroys their crystalline structure. This process, known as gelatinization, is necessary to allow access to the amylose and amylopectin polymers by the enzymes (α-amylases) that initiate their digestion in the mouth and small intestine. Without prior cooking and gelatinization, digestion of starch occurs at a greatly reduced rate, and may not be complete. Alpha-amylases cleave α 1-4 bonds in amylase and amylopectin to release glucose dimers (maltose), trimers (maltotriose) and other small glucose oligomers. Maltose and small linear glucose oligomers are subsequently fully digested to glucose by the maltase-glucoamylase enzyme system on the villous (brush border) surface of intestinal lining cells (enterocytes). Branched oligomers (containing α 1-6 bonds not cleaved by α-amylases) are digested to glucose monomers by another brush border enzyme system known as sucrase-isomaltase. Free glucose monomers generated as a result of the combined action of all of the aforementioned enzymes is then transported into the enterocytes by the sodium glucose linked transporter (SGLT) on the enterocyte surface. SGLT is a co-transporter that is driven by the sodium gradient between the intestinal lumen and cell cytoplasm, and moves one glucose molecule into the cell for every two sodium ions transported. Once glucose is so transported through the luminal, or apical surface of the cell, it is then transported out of the cell on the opposite (basolateral) side, by GLUT2 transporters to the submucosal space, from where glucose enters capillaries to reach the bloodstream.

While not wishing to be bound by any specific theory, it is believed that nanocellulose and other biopolymers disclosed herein can interfere with the complex process described herein in a variety of ways. First, it may bind to gelatinized starch granules to prevent access of α-amylases to the amylopectin and amylose at the surface of the granule. In the case of uncooked starch, nanocellulose can further increase the difficulty of digestion by preventing gelatinization within the GIT or again by preventing access of amylases to the limited amounts of potentially accessible amylose and amylopectin. Nanocellulose may also interact with α-amylases to alter their activity, which can occur in a number of ways, including sequestration of the enzymes within a mesh or hydrogel of nanocellulose, binding to and blocking of the active enzymatic site, or binding outside the active site in a way that alters the 3D conformation and thus activity of the active site. Nanocellulose may also bind to the mucous layer that covers the intestinal enterocytes, potentially increasing its viscosity, or otherwise reducing access of maltose and other glucose oligomer products of α-amylase digestion to the maltase-glucoamylase and/or sucrase-isomaltase enzyme systems. In addition, nanocellulose may bind to and alter the activity of the maltase-glucoamylase or sucrase-isomaltase enzymes. Finally, nanocellulose may bind to and alter the activity of the SGLT transporter. By any one or a combination of these mechanisms, or by other unknown mechanisms, ingestion of nanocellulose prior to or along with a high starch meal, may reduce starch digestion to glucose and/or absorbance of glucose produced, and thus reduce the caloric and glycemic load resulting from the starch meal.

What is claimed is:

1. A method for reducing the bioavailability and/or absorption of ingested fat from foodstuff in a subject, the method comprising:
    administering an amount of a suspension of a nanobiopolymer, or combinations of nanobiopolymers, sufficient to reduce the bioavailability ingested fat to a subject,
    wherein the nanobiopolymer is selected from the group consisting of cellulose nanofibers or cellulose nanocrystals and combinations thereof,
    wherein, when the nanobiopolymer is cellulose nanofibers, the nanobiopolymer comprises fibrillar nanocellulose made by mechanical milling and having a diameter of up to 100 nm,
    wherein when the nanobiopolymer is cellulose nanocrystals, the cellulose nanocrystals comprise nanocrystalline cellulose made by chemical means and the nanocrystalline cellulose ranges in diameter from 1 nm to 250 nm and
    further wherein the bioavailability of the ingested fat is reduced by at least 30%.

2. The method of claim 1, wherein the nanobiopolymer is incorporated into the foodstuff;
    is administered separately from the foodstuff;
    or is incorporated into the foodstuff and is administered separately from the foodstuff.

3. The method of claim 1, wherein the amount of a nanobiopolymer sufficient to reduce the bioavailability and/or absorption of ingested fat from foodstuff is from about 0.75% to about 1.5% by weight of the foodstuff.

4. The method of claim 1, wherein the fat comprises triglycerides.

5. The method of claim 1, wherein the bioavailability and/or absorption of ingested fat is reduced by a reduction in translocation, in the subject's intestinal epithelium, of free fatty acids from triglycerides.

6. The method of claim 1, wherein the bioavailability and/or absorption of ingested fat is reduced by modulating pancreatic lipase activity.

7. The method of claim 1, wherein the bioavailability and/or absorption of ingested fat is reduced by inhibiting the hydrolysis of triglycerides.

8. The method of claim 1, wherein the subject is a human subject.

9. The method of claim 1, wherein the bioavailability of the ingested fat is reduced by at least 50%.

* * * * *